United States Patent
Anglada et al.

(10) Patent No.: US 10,072,000 B2
(45) Date of Patent: Sep. 11, 2018

(54) METHOD OF TREATING INSOMNIA WITH HALOGENATED PYRAZOLO[1,5-A]PYRIMIDINES

(71) Applicant: FERRER INTERNACIONAL, S.A., Barcelona (ES)

(72) Inventors: Luis Anglada, Barcelona (ES); Albert Palomer, Barcelona (ES); Antonio Guglietta, Barcelona (ES)

(73) Assignee: FERRER INTERNACIONAL, S.A., Barcelona (ES)

( * ) Notice: Subject to any disclaimer, the term of this patent is extended or adjusted under 35 U.S.C. 154(b) by 433 days.

(21) Appl. No.: 13/965,516

(22) Filed: Aug. 13, 2013

(65) Prior Publication Data

US 2013/0331401 A1 Dec. 12, 2013
US 2016/0368912 A9 Dec. 22, 2016

Related U.S. Application Data

(62) Division of application No. 11/922,602, filed as application No. PCT/EP2006/063243 on Jun. 15, 2006, now Pat. No. 8,530,482.

(60) Provisional application No. 60/692,866, filed on Jun. 21, 2005.

(30) Foreign Application Priority Data

Jun. 21, 2005 (EP) ..................... 05105478

(51) Int. Cl.
| | | |
|---|---|---|
| *A61K 31/519* | (2006.01) | |
| *C07D 471/04* | (2006.01) | |
| *C07C 233/33* | (2006.01) | |
| *C07D 487/04* | (2006.01) | |
| *C07C 231/12* | (2006.01) | |
| *C07C 233/43* | (2006.01) | |
| *C07C 303/40* | (2006.01) | |
| *C07C 311/08* | (2006.01) | |

(52) U.S. Cl.
CPC .......... *C07D 471/04* (2013.01); *A61K 31/519* (2013.01); *C07C 231/12* (2013.01); *C07C 233/33* (2013.01); *C07C 233/43* (2013.01); *C07C 303/40* (2013.01); *C07C 311/08* (2013.01); *C07D 487/04* (2013.01)

(58) Field of Classification Search
CPC .................................................. A61K 31/519
See application file for complete search history.

(56) References Cited

U.S. PATENT DOCUMENTS

| | | |
|---|---|---|
| 4,521,422 A | 6/1985 | Dusza et al. |
| 6,399,621 B1 | 6/2002 | Dusza et al. |
| 8,530,482 B2 * | 9/2013 | Anglada et al. ........... 514/259.3 |

| | | |
|---|---|---|
| 2006/0063784 A1 | 3/2006 | Wang et al. |
| 2006/0063785 A1 | 3/2006 | Wang et al. |
| 2006/0189633 A1 | 8/2006 | Huang et al. |

FOREIGN PATENT DOCUMENTS

| | | | |
|---|---|---|---|
| WO | WO 2005/014597 A | | 2/2005 |
| WO | WO 2005014597 A1 | * | 2/2005 |
| WO | WO 2006/136530 A1 | | 12/2006 |
| WO | WO 2006136530 A1 | * | 12/2006 |

OTHER PUBLICATIONS

MeSH entry for Sleep Disorders; http://www.ncbi.nlm.nih.gov/mesh/68012893; accessed Mar. 25, 2015.*
Sleep Disorders Guide; http://www.sleepdisordersguide.com/topics/nocturnal-myoclonus.html, accessed Mar. 25, 2015.*
Horoszok et al.; "A single-dose, randomized, double-blind, double dummy, placebo and positive controlled, five-way cross-over study to assess the pharmacodynamic effects of lorediplon in a phase advance model of insomnia in healthy Caucasian adult male subjects"; 2014; Hum. Psychopharmacol.; 29(3): 266-73; PubMed abstract; PMID: 24911577.*
Adis R&D Profile; "Indiplon: Indiplon modified-release, Indiplon MR, NBI 34060, NBI 34060 modified-release, NBI 34060 MR"; 2002; Durgs R&D; 3(3): 197-199.*
Ismail; "Review: Important fluorinated drugs in experimental and clinical use"; 2002; Journal of Fluorine Chemistry; 118: 27-33.*

(Continued)

*Primary Examiner* — Timothy P Thomas
(74) *Attorney, Agent, or Firm* — Birch, Stewart, Kolasch & Birch, LLP

(57) ABSTRACT

The invention provides novel halogenated pyrazolo[1,5-a]pyrimidines of formula (I) wherein R, $R_1$, X and Y have different meanings, and pharmaceutically acceptable salts thereof. Compounds of formula (I) are useful for treating or preventing anxiety, epilepsy and sleep disorders including insomnia, and for inducing sedation-hypnosis, anesthesia, sleep and muscle relaxation. The invention also provides synthetic procedures for preparing said compounds and certain intermediates, as well as intermediates themselves.

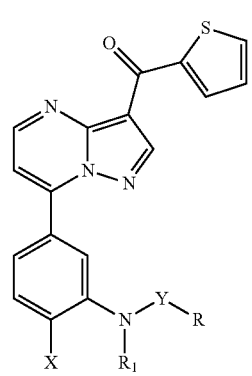

(I)

8 Claims, No Drawings

(56) References Cited

OTHER PUBLICATIONS

Horoszok et al.; "A single-dose, randomized, double-blind, double dummy, placebo and positive-controlled, five-way cross-over study to assess the pharmacodynamics effects of lorediplon in a phase advance model of insomnia in healthy Caucasian adult male subjects"; 2014; Hum. Psychopharmacol. Clin. Exp.; 29: 266-273.*
Patani et al.; Bioisosterism: A rational Approach in Drug Design; 1996; Chem. Rev.; 96:3147-3176.*
Ismail; "Review: Important fluorinated drugs in experimental and clinical use"; 2002; Journal of Fluorine Chemistry; 118: 27-33.*
Encyclopedia Britannica, "Solid, "http://www.britannica.com/EBchecked/topic/553257/solid, last accessed on Mar. 23, 2012.
Final Office Action dated Apr. 14, 2011, issued in U.S. Appl. No. 11/922,602.
International Search Report dated Sep. 28, 2006 for International Application No. PCT/EP2006/063243 (PCT/ISA/210).
Non-Final Office Action dated Aug. 23, 2010, issued in U.S. Appl. No. 11/922,602.
Non-Final Office Action dated Dec. 9, 2010, issued in U.S. Appl. No. 11/922,602.
Notice of Allowability dated May 10, 2013, issued in U.S. Appl. No. 11/922,602.
Office Action dated Mar. 30, 2012 for U.S. Appl. No. 12/513,884.

* cited by examiner

METHOD OF TREATING INSOMNIA WITH HALOGENATED PYRAZOLO[1,5-A]PYRIMIDINES

This application is a Divisional Application of U.S. patent application Ser. No. 11/922,602, filed Sep. 12, 2008, which is the U.S. National Phase of PCT/EP2006/063243, filed Jun. 15, 2006, which claims benefit of Provisional Application No. 60/692,866 filed on Jun. 21, 2005. This application also claims priority under 35 U.S.C. §119(a) to European Patent Application No. 05105478.1, filed in Europe on Jun. 21, 2005, the entire contents of which are hereby incorporated by reference.

TECHNICAL FIELD

This invention is directed to agents with affinity for $GABA_A$ receptor, specifically to halogenated pyrazolo[1,5-a]pyrimidines, and more specifically to [7-(3-amino-4-halo-phenyl)-pyrazolo[1,5-a]pyrimidin-3-yl]-thiophen-2-yl-methanone acyl and sulfonyl compounds.

BACKGROUND OF THE INVENTION $GABA_A$ receptor (γ-aminobutyric acid$_A$) is a pentameric protein which forms a membrane ion channel. $GABA_A$ receptor is implicated in the regulation of sedation, anxiety, muscle tone, epileptogenic activity and memory functions. These actions are due to defined subunits of $GABA_A$ receptor, particularly the $\alpha_1$- and $\alpha_2$-subunits.

Sedation is modulated by the $\alpha_1$-subunit. Zolpidem is characterized by a high affinity for the $\alpha_1$-receptors and its sedative and hypnotic action is mediated by these receptors in vivo. Similarly, the hypnotic action of zaleplon is also mediated by the $\alpha_1$-receptors.

The anxiolytic action of diazepam is mediated by the enhancement of GABAergic transmission in a population of neurons expressing the $\alpha_2$-receptors. This indicates that the $\alpha_2$-receptors are highly specific targets for the treatment of anxiety.

Muscle relaxation in diazepam is mainly mediated by $\alpha_2$-receptors, since these receptors exhibit a highly specific expression in spinal cord.

The anticonvulsant effect of diazepam is partly due to $\alpha_1$-receptors. In diazepam, a memory-impairing compound, anterograde amnesia is mediated by $\alpha_1$-receptors.

$GABA_A$ receptor and its $\alpha_1$- and $\alpha_2$-subunits have been widely reviewed by H. Mohler et al. (J. Pharmacol. Exp. Ther., 300, 2-8, 2002); H. Mohler et al. (Curr. Opin. Pharmacol., 1, 22-25, 2001); U. Rudolph et al. (Nature, 401, 796-800, 1999); and D. J. Nutt et al. (Br. J. Psychiatry, 179, 390-396, 2001).

Diazepam and other classical benzodiazepines are extensively used as anxiolytic agents, hypnotic agents, anticonvulsants and muscle relaxants. Their side effects include anterograde amnesia, decrease in motor activity and potentiation of ethanol effects.

In this context, the compounds of this invention are ligands of $\alpha_1$- and $\alpha_2$-$GABA_A$ receptor for their clinical application in sleep disorders, preferably insomnia, anxiety and epilepsy.

Insomnia is a highly prevalent disease. Its chronicity affects 10% of the population and 30% when transitory insomnia is computed as well. Insomnia describes the trouble in getting to sleep or staying asleep and is associated with next-day hangover effects such as weariness, lack of energy, low concentration and irritability. The social and health impact of this complaint is important and results in evident socioeconomic repercussions.

Pharmacological therapy in the management of insomnia firstly included barbiturates and chloral hydrate, but these drugs elicit numerous known adverse effects, for example, overdose toxicity, metabolic induction, and enhanced dependence and tolerance. In addition, they affect the architecture of sleep by decreasing above all the duration and the number of REM sleep stages. Later, benzodiazepines meant an important therapeutic advance because of their lower toxicity, but they still showed serious problems of dependence, muscle relaxation, amnesia and rebound insomnia following discontinuation of medication.

The latest known therapeutic approach has been the introduction of non-benzodiazepine hypnotics, such as pyrrolo[3,4-b]pyrazines (zopiclone), imidazo[1,2-a]pyridines (zolpidem) and, finally, pyrazolo[1,5-a]pyrimidines (zaleplon). Later, two new pyrazolo[1,5-a]pyrimidines, indiplon and ocinaplon, have entered into development, the latter with rather anxiolytic action. All these compounds show a rapid sleep induction and have less next-day hangover effects, lower potential for abuse and lower risk of rebound insomnia than benzodiazepines. The mechanism of action of these compounds is the alosteric activation of $GABA_A$ receptor through its binding to benzodiazepine binding site (C. F. P. George, The Lancet, 358, 1623-1626, 2001). While benzodiazepines are unspecific ligands at $GABA_A$ receptor binding site, zolpidem and zaleplon show a greater selectivity for $\alpha_1$-subunit. Notwithstanding that, these drugs still affect the architecture of sleep and may induce dependence in long-term treatments.

The present invention is structurally related to, but patentably distinct from the compound N-{3-[3-(thiophene-2-carbonyl)-pyrazolo[1,5-a]pyrimidin-7-yl]-phenyl}-N-methyl-acetamide, indiplon, which is described in U.S. Pat. No. 6,399,621, and the compounds N-{3-[3-(thiophene-2-carbonyl)-pyrazolo[1,5-a]pyrimidin-7-yl]-phenyl}-N-methyl-methanesulfonamide and N-{3-[3-(thiophene-2-carbonyl)-pyrazolo[1,5-a]pyrimidin-7-yl]-phenyl}-N-prop-2-ynyl-methanesulfonamide, which are described in WO 2005014597, examples 3 and 16 respectively, because of their improved properties as shown in the Detailed Description of the Invention. Similar compounds to indiplon had been disclosed previously in U.S. Pat. No. 4,521,422.

Research for new active compounds in the management of insomnia answers an underlying health need, because even recently introduced hypnotics still affect the architecture of sleep and may induce dependence in long-term treatments.

It is therefore desirable to focus on the development of new hypnotic agents with a lower risk of side effects.

Thus, the present invention is directed to new halogenated pyrazolo[1,5-a]pyrimidines which are active versus $GABA_A$ and, particularly, versus its $\alpha_1$- and $\alpha_2$-subunits. Consequently, the compounds of this invention are useful in the treatment and prevention of all those diseases mediated by $GABA_A$ receptor $\alpha_1$- and $\alpha_2$-subunits. Non-limitative examples of such diseases are sleep disorders, preferably insomnia, anxiety and epilepsy. Non-limitative examples of the relevant indications of the compounds of this invention are all those diseases or conditions, such as insomnia or anesthesia, in which an induction of sleep, an induction of sedation or an induction of muscle relaxation are needed.

SUMMARY OF THE INVENTION

The present invention describes a novel class of compounds represented by formula (I):

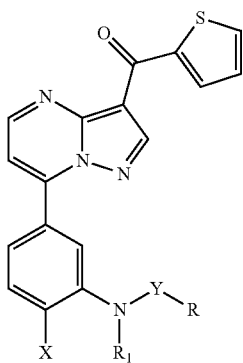

and pharmaceutically acceptable salts thereof, wherein R, $R_1$, X and Y are defined below, which are ligands of $GABA_A$ receptor.

It is another object of this invention to provide novel methods of treating or preventing anxiety, epilepsy and sleep disorders including insomnia, and for inducing sedation-hypnosis, anesthesia, sleep and muscle relaxation by administering a therapeutically effective amount of a compound of formula (I) or a pharmaceutically acceptable salt thereof. Synthetic procedures for preparing said compounds and certain intermediates are also within the scope of the invention. Relevant intermediates themselves also constitute another object of the invention.

DETAILED DESCRIPTION OF THE INVENTION

The present invention relates to novel [7-(3-amino-4-halophenyl)-pyrazolo[1,5-a]pyrimidin-3-yl]-thiophen-2-yl-methanone acyl and sulfonyl compounds of formula (I):

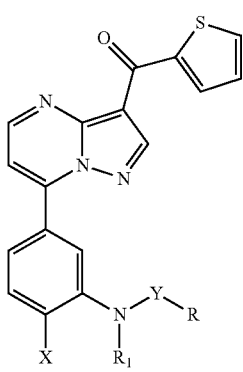

wherein

R represents an alkyl($C_1$-$C_6$);

$R_1$ is selected from the group consisting of alkyl($C_1$-$C_6$) and alkynyl($C_1$-$C_6$);

X represents a halogen atom; and

Y is selected from the group consisting of —CO— and —$SO_2$—; and a pharmaceutically acceptable salt thereof.

Preferably R is methyl; $R_1$ is selected from methyl and prop-2-ynyl; and X is selected from fluorine and chlorine.

The term "pharmaceutically acceptable salt" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluene-sulfonic, succinic, tartaric acids and the like.

The present invention comprises the compounds:

N-{2-fluoro-5-[3-(thiophene-2-carbonyl)-pyrazolo[1,5-a]pyrimidin-7-yl]-phenyl}-N-methyl-acetamide;

N-{2-chloro-5-[3-(thiophene-2-carbonyl)-pyrazolo[1,5-a]pyrimidin-7-yl]-phenyl}-N-methyl-acetamide;

N-{2-fluoro-5-[3-(thiophene-2-carbonyl)-pyrazolo[1,5-a]pyrimidin-7-yl]-phenyl}-N-methyl-methanesulfonamide;

N-{2-chloro-5-[3-(thiophene-2-carbonyl)-pyrazolo[1,5-a]pyrimidin-7-yl]-phenyl}-N-methyl-methanesulfonamide; and N-{2-fluoro-5-[3-(thiophene-2-carbonyl)-pyrazolo[1,5-a]pyrimidin-7-yl]-phenyl}-N-prop-2-ynyl-methanesulfonamide.

Another embodiment of the present invention is to provide a process for preparing the compounds of formula (I) and their pharmaceutically acceptable salts.

The compounds of the present invention can be used for treating or preventing diseases associated with $GABA_A$ receptor modulation in a mammal which comprises administering to said mammal in need thereof an effective amount of a compound of formula (I) or a pharmaceutically acceptable salt thereof. More specifically, diseases associated with $GABA_A$ receptor modulation comprise diseases associated with $\alpha_1$-$GABA_A$ receptor modulation and/or $\alpha_2$-$GABA_A$ receptor modulation. A non-limitative list of such diseases comprises anxiety, epilepsy, sleep disorders, including insomnia, and the like.

Another embodiment of the present invention is to provide the use of a compound of formula (I) for treating or preventing anxiety in a mammal in need thereof which comprises administering to said mammal an effective amount of said compound or a pharmaceutically acceptable salt thereof.

Another embodiment of the present invention is to provide the use of a compound of formula (I) for treating or preventing epilepsy in a mammal in need thereof which comprises administering to said mammal an effective amount of said compound or a pharmaceutically acceptable salt thereof.

Another embodiment of the present invention is to provide the use of a compound of formula (I) for treating or preventing sleep disorders in a mammal in need thereof which comprises administering to said mammal an effective amount of said compound or a pharmaceutically acceptable salt thereof.

Another embodiment of the present invention is to provide the use of a compound of formula (I) for treating or preventing insomnia in a mammal in need thereof which comprises administering to said mammal an effective amount of said compound or a pharmaceutically acceptable salt thereof.

Another embodiment of the present invention is to provide the use of a compound of formula (I) for inducing sedation-hypnosis in a mammal in need thereof which comprises administering to said mammal an effective amount of said compound or a pharmaceutically acceptable salt thereof.

Another embodiment of the present invention is to provide the use of a compound of formula (I) for inducing anesthesia in a mammal in need thereof which comprises administering to said mammal an effective amount of said compound or a pharmaceutically acceptable salt thereof.

Another embodiment of the present invention is to provide the use of a compound of formula (I) for modulating the necessary time to induce sleep and its duration in a mammal in need thereof which comprises administering to said mammal an effective amount of said compound or a pharmaceutically acceptable salt thereof.

Another embodiment of the present invention is to provide the use of a compound of formula (I) for inducing muscle relaxation in a mammal in need thereof which comprises administering to said mammal an effective amount of said compound or a pharmaceutically acceptable salt thereof.

The present invention also relates to a method of treatment or prevention of a mammal suffering from diseases associated with $GABA_A$ receptor modulation in a mammal, which comprises administering to said mammal in need thereof a therapeutically effective amount of a compound of formula (I) or a pharmaceutically acceptable salt thereof, together with pharmaceutically acceptable diluents or carriers. More specifically, diseases associated with $GABA_A$ receptor modulation comprise diseases associated with $\alpha_1$-$GABA_A$ receptor modulation and/or $\alpha_2$-$GABA_A$ receptor modulation. A non-limitative list of such diseases comprises anxiety, epilepsy, sleep disorders, including insomnia, and the like.

As used herein, the term "mammal" shall refer to the Mammalia class of higher vertebrates. The term "mammal" includes, but is not limited to, a human.

Another embodiment of the present invention is to provide a pharmaceutical composition containing a compound of formula (I) or a pharmaceutically acceptable salt thereof in association with therapeutically inert carriers.

Another embodiment of the present invention is to provide a process for preparing intermediate compounds of formula (VI):

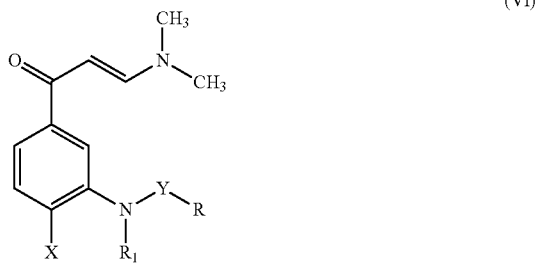

(VI)

wherein R, $R_1$, X and Y are as defined above.

The specific intermediate compounds (VI), namely:
N-[5-(3-dimethylamino-acryloyl)-2-fluoro-phenyl]-N-methyl-acetamide;
N-[2-chloro-5-(3-dimethylamino-acryloyl)-phenyl]-N-methyl-acetamide;
N-[5-(3-dimethylamino-acryloyl)-2-fluoro-phenyl]-N-methyl-methanesulfonamide;
N-[2-chloro-5-(3-dimethylamino-acryloyl)-phenyl]-methyl-methanesulfonamide, and
N-[5-(3-dimethylamino-acryloyl)-2-fluoro-phenyl]-N-prop-2-ynyl-methanesulfonamide constitute another embodiment of the invention.

The compositions include those suitable for oral, rectal and parenteral (including subcutaneous, intramuscular, and intravenous) administration, although the most suitable route will depend on the nature and severity of the condition being treated. The most preferred route of the present invention is the oral route. The compositions may be conveniently presented in unit dosage form, and prepared by any of the methods well known in the art of pharmacy.

The active compound can be combined with a pharmaceutical carrier according to conventional pharmaceutical compounding techniques. The carrier may take a wide variety of forms depending on the form of the preparation desired for administration, e.g. oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubri-cants, binders, disintegrating agents and the like, in the case of oral solid preparations (such as for example, powders, capsules, and tablets) with the oral solid preparations being preferred over the oral liquid preparations.

Because of their ease of administration, tablets and capsules represent the most advantageous oral dosage unit form, in which case solid pharmaceutical carriers are employed. If desired, tablets may be coated by standard aqueous or nonaqueous techniques.

A suitable dosage range for use is from about 0.01 mg to about 100.00 mg total daily dose, given as a once daily administration or in divided doses if required.

The compounds of general formula (I) may be prepared according to the reaction shown in Scheme 1.

Scheme 1

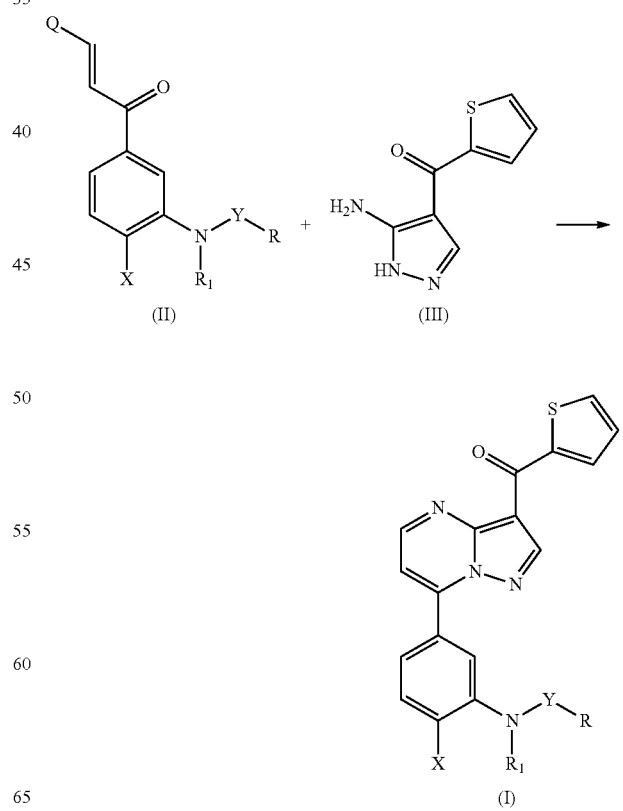

In the intermediates of formula (II), R, $R_1$, X and Y are as defined in (I) and Q is an appropriate leaving group selected from the group consisting of N(dialkyl($C_1$-$C_6$)), alkylthio ($C_1$-$C_6$) and alkoxy($C_1$-$C_6$). Preferably Q is selected from the group consisting of dimethylamino, methylthio and methoxy. The treatment of the resulting compounds in the form of free base with an acid affords the corresponding salt thereof.

The reaction of aminopyrazole (III) with appropriately substituted 1-aryl-2-propen-1-one (II) is carried out in an inert polar protic or aprotic solvent such as glacial acetic acid, ethanol, methanol, dimethylformamide or dimethylsulfoxide at a temperature ranging from 50° to 130° C. After elapsing several hours (reaction time), the solvent is removed and the residue obtained is partitioned between an aqueous solution of sodium bicarbonate and dichloromethane. The crude resulting from evaporating the organic layer to dryness may be purified by one of the following methods: (a) silica gel chromatography using ethyl acetate or dichloromethane/methanol as eluent; or (b) crystallization in a suitable solvent (ethyl acetate, ethanol, methanol, etc.).

The intermediate of formula (II) when Q is dimethylamino [intermediate (VI)] can be obtained following the reaction sequence shown in Scheme 2.

The intermediates of formula (II), when Q is dimethylamino, Y is sulfonyl and $R_1$ is methyl [intermediates (VII)], can alternatively be prepared according to Scheme 3.

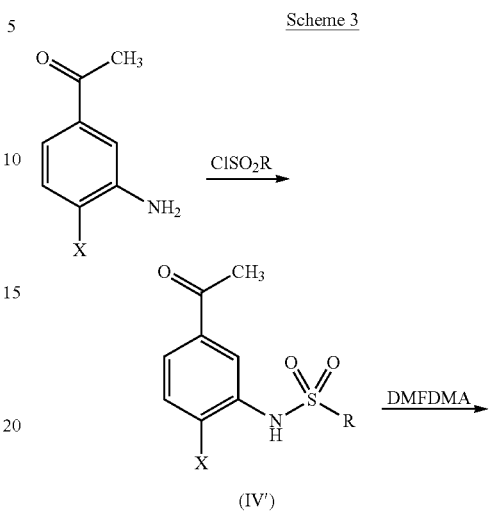

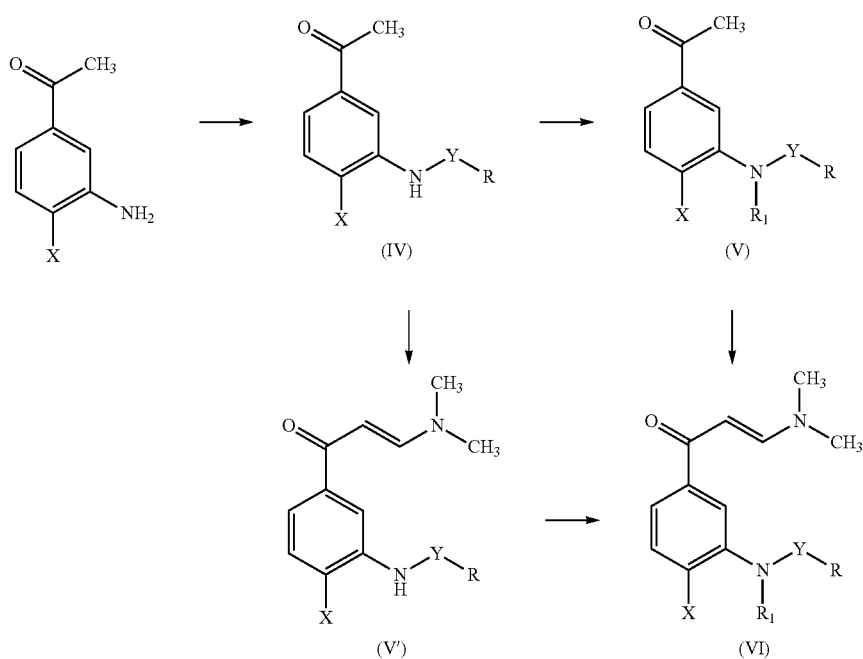

wherein R, $R_1$, X and Y are as described above.

The intermediates of formula (IV) when Y is a sulfonyl group [intermediates (IV')] are prepared according to the method described by R. H. Uloth et al (J. Med. Chem. 9, 88-96, 1966).

The aviation of the intermediates (IV) leading to the intermediates of formula (V) is performed via formation of an anion and subsequent reaction with an alkyl halide.

The enaminones of formula (V') and (VI) are prepared by reacting the corresponding acetophenones (IV) and (V) respectively with N,N-dimethylformamide dimethylacetal (DMFDMA) or Bredereck's reagent (ten-butoxybis(dimethylamino)methane).

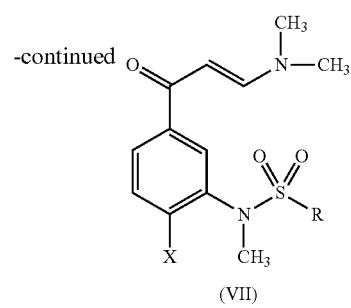

The conversion of (IV') into (VII) leads to the formation of the enaminone and, simultaneously, the formation of the N-methyl-sulfonamide as a result of the use of the properties of the N,N-dimethylformamide dimethyl acetal as a methylating agent.

The intermediates of formula (II), when Q is dimethylamino and $R_1$ is methyl (X), can also be prepared according to Scheme 4.

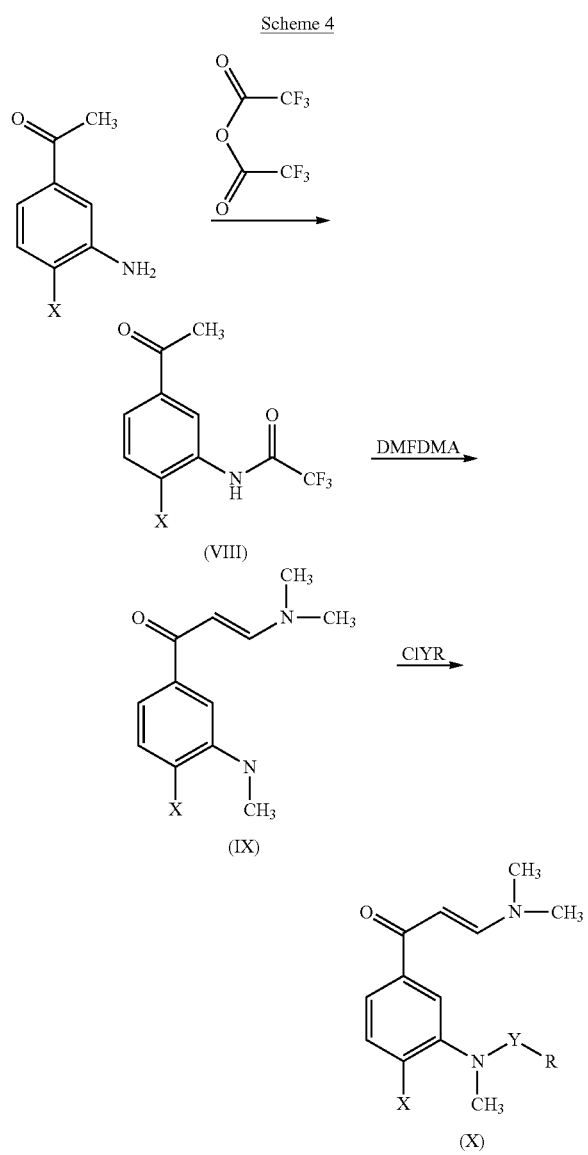

The advantage of this process is based on the fact that the formation of the sulfonamide or carboxamide takes place in the last step of the process. As a result, the total number of reaction steps is reduced in the preparation of large series of products. Moreover, as shown in the scheme, the conversion of (VIII) into (IX) leads to three following reactions in a one-pot process: (a) formation of the enaminone; (b) methylation of the trifluoroacetamide; and (c) deacylation yielding the N-methylated amine. The subsequent reaction of (IX) with the corresponding sulfonic acid or carboxylic acid chloride leads to obtaining intermediates (X).

The compounds of the present invention have a high affinity for $\alpha_1$- and $\alpha_2$-$GABA_A$ receptors. These in vitro results are consistent with those in vivo results obtained in sedation-hypnosis tests.

In accordance with the results obtained, the compounds of the present invention have evidenced pharmacological activity both in vitro and in vivo, which has been similar to or higher than that of prior-art compounds. All these results support their use in diseases or conditions modulated by $\alpha_1$- and $\alpha_2$-$GABA_A$ receptors, such as insomnia or anesthesia, in which an induction of sleep, an induction of sedation or an induction of muscle relaxation are needed. Furthermore, it has been found that administering the compounds of the present invention at low doses a surprising increase in the sedative-hypnotic activity is achieved over the one achieved using the compounds of the prior art (i.e. Indiplon, Zaleplon and Examples 3 and 16 from WO200501497), as it is illustrated below.

Pharmacological and cytotoxic activities, metabolic stability and pharmacokinetic profile of the compounds of the present invention have been determined as shown below.

a) Pharmacological Activities

1—Ligand-Binding Assays. Determination of the Affinity of Test Compounds for $\alpha_1$- and $\alpha_2$-$GABA_A$ Receptor Male Sprague-Dawley rats weighing 200-250 g at the time of experiment were used. After decapitation, the cerebellum (tissue that mostly contains $\alpha_1$-$GABA_A$ receptor) and spinal cord (tissue that mostly contains $\alpha_2$-$GABA_A$ receptor) were removed. The membranes were prepared according to the method by J. Lameh et al. (Prog. Neuro-Psychopharmacol. Biol. Psychiatry, 24, 979-991, 2000) and H. Noguchi et al. (Eur J Pharm, 434, 21-28, 2002) with slight modifications. Once the tissues weighed, they were suspended in 50 mM Tris.HCl (pH 7.4), 1:40 (v/v), or sucrose 0.32 M in the case of spinal cord, homogenized and then centrifuged at 20000 g for 10 min at 7° C. The resulting pellet was resuspended under the same conditions and centrifuged again. The pellet was finally resuspended on a minimum volume and kept at −80° C. overnight. On the next day, the process was repeated until the final pellet was resuspended at a ratio of 1:10 (v/v) in the case of cerebellum and at a ratio of 1:5 (v/v) in the case of spinal cord.

Affinity was determined by competitive tests using radiolabeled flumazenil as ligand. The tests were performed according to the methods described by S. Arbilla et al. (Eur. J. Pharmacol., 130, 257-263, 1986); and Y. Wu et al. (Eur. J. Pharmacol., 278, 125-132, 1995) using 96-well microtiter plates. The membranes containing the study receptors, flumazenil (radiolabeling at a final concentration of 1 nM) and ascending concentrations of test compounds (in a total volume of 230 μl in 50 mM [ph 7.4] Tris.HCl buffer) were incubated. Simultaneously, the membranes were only incubated with the radiolabeled flumazenil (total binding, 100%) and in the presence of an elevated concentration of unradiolabeled flumazenil (non-specific binding, % estimation of radiolabeled ligand). The reactions started on adding the radiolabeled ligand followed by incubation for 60 minutes at 4° C. At the end of the incubation period, 200 μl of reaction were transferred to a multiscreen plate (Millipore) and filtered using a vacuum manifold and then washed three times with cold test buffer. The multiscreen plates were equipped with a GF/B filter that retained the membranes containing the receptors and the radiolabeled ligand which had been bound to the receptors. After washing, the plates were left till dry. Once dried, scintillation liquid was added and left under stirring overnight. The next day the plates were counted using a Perkin-Elmer Microbeta scintillation counter.

For analysis of the results the percentage of specific binding for every concentration of test compound was calculated as follows:

% specific binding=$(X-N/T-N) \times 100$ where,

X: amount of bound ligand for every concentration of compound.

T: total binding, maximum amount bound to the radiolabeled ligand.

N: non-specific binding, amount of radiolabeled ligand bound in a non-specific way irrespective of the receptor used.

Every concentrations of each compound were tested in triplicate and their mean values were used to determine the experimental values of % specific binding versus the concentration of compound. Affinity data are expressed as % inhibition at $10^{-5}M$ and $10^{-7}M$ concentrations and Ki obtained in some compounds, in which the ratios between $\alpha_1$ and $\alpha_2$ affinities were calculated. The results of these tests are given in Tables 1 and 2. Advantageously, certain compounds of the present invention show a higher selectivity as sedative-hypnotic agents towards the muscle relaxing activity as evidenced by an enhanced $\alpha_2/\alpha_1$ ratio as compared to the prior art compounds.

TABLE 1

Affinity for the $\alpha_1$ subunit of GABA$_A$ receptor

| Compound | % Inhib $10^{-5}M$ | % Inhib $10^{-7}M$ | Ki (nM) |
| --- | --- | --- | --- |
| Preparative example 2 | 100.4 | 95.3 | 2.1 |
| Preparative example 4 | 99.8 | 60.0 | 57.6 |
| Preparative example 6 | 99.7 | 88.8 | 1.7 |
| Preparative example 8 | 93.8 | 40.9 | — |
| Preparative example 10 | 100.0 | 99.7 | 0.98 |
| Indiplon | | | 3.1 |
| Zaleplon | 97.2 | 26.1 | 151.4 |
| Example 3 WO2005014597 | 100.4 | 90.6 | 7.4 |
| Example 16 WO2005014597 | 100.0 | 99.9 | 1.3 |

TABLE 2

Affinity for the $\alpha_2$ subunit of GABA$_A$ receptor

| Compound | % Inhib $10^{-5}M$ | % Inhib $10^{-7}M$ | Ki (nM) |
| --- | --- | --- | --- |
| Preparative example 2 | 99.3 | 67.3 | 20.0 |
| Preparative example 4 | 95.7 | 8.4 | 197.8 |
| Preparative example 6 | 97.9 | 55.9 | 11.2 |
| Preparative example 8 | 68.9 | 0.0 | — |
| Preparative example 10 | 100.2 | 97.5 | 1.6 |
| Indiplon | 99.2 | 65.7 | 23.8 |
| Zaleplon | 78.7 | — | 1528.1 |
| Example 3 WO2005014597 | 99.8 | 58.5 | 36.7 |
| Example 16 WO2005014597 | 100.2 | 87.2 | 22.0 |

In this context, the selectivity $\alpha_2/\alpha_1$ ratio for the compound from preparative example 2 is 9.6 in contrast to 7.7 for indiplon and 5.0 for the compound from example 3 in WO2005014597, thus resulting in 25% and 92% increased selectivity respectively. Consequently less side effects are expected for the present compounds.

2—In Vivo Determination of Predictive Sedative-Hypnotic Action

The in vivo effects of these compounds were assessed by a predictive sedation-hypnosis test in mice (D. J. Sanger et al., Eur. J. Pharmacol., 313, 35-42, 1996; and G. Griebel et al., Psychopharmacology, 146, 205-213, 1999).

Groups of 5-8 male CD1 mice, weighing 22-26 g at the time of testing, were used. The test compounds were administered in single equimolecular intraperitoneal doses, suspended in 0.25% agar with one drop of Tween 80 in a volume of 10 ml/kg. Two doses were tested in each route. Control animals received the vehicle alone. Using a Smart System (Panlab, S. L., Spain) the traveled distance in cm was recorded for each mouse at 5-min intervals during a period of 30 minutes after intraperitoneal (ip) dosing and 60 minutes after oral (po) dosing. The inhibition percentage of traveled distance of treated animals versus control animals (the first 5 min were discarded) was calculated. The results of this test are given in Table 3.

TABLE 3

Determination of in vivo sedative-hypnotic activity in mice.

| | % Inhib motor activity | | | |
| --- | --- | --- | --- | --- |
| | Ip | | po | |
| Compound | 98 μmol/kg | 0.98 μmol/kg | 98 μmol/kg | 3 μmol/kg |
| Preparative example 2 | 94.97 | 81.21 | 92.29 | 84.01 |
| Preparative example 4 | 90.26 | — | 88.71 | — |
| Preparative example 6 | 91.5 | 69.42 | 82.00 | 46.23 |
| Preparative example 8 | 78.26 | — | — | — |
| Preparative example 10 | 91.6 | 91.94 | 90.22 | 47.89 |
| Indiplon | 88.04 | 70.45 | 82.40 | 73.67 |
| Zaleplon | 84.98 | 32.67 | 64.11 | 25.39 |
| Example 3 WO2005014597 | 89.76 | 64.56 | — | — |
| Example 16 WO2005014597 | 95.36 | 71.43 | 84.33 | 38.78 |

Surprisingly, relevant compounds in the present invention show an increased sedative-hypnotic activity comparatively to prior art compounds.

Particularly, the compounds of the present invention at low doses give rise to a higher increase in the sedative-hypnotic activity over the one achieved using the compounds of the prior art (i.e. Indiplon, Zaleplon and Examples 3 and 16 from WO2005014597). This is of great importance since it is possible to get the desired therapeutic effect (i.e. sedative-hypnotic) using a lower dose with the subsequent advantage that the related side-effects can be minimized.

The comparison between the compounds of the present invention and the corresponding compounds of the prior art, shows that the presence of a halogen atom in the structure represented by the formula (I) gives rise to an increase in the sedative-hypnotic activity, especially at low doses. Thus, for instance, comparing the activity of compound of Example 10 of the present invention with that obtained with the compound of Example 16 of WO2005014597, an increase higher than 20% is achieved when a low dose is used, independently of the administration route.

b) Cytotoxic Activity

In Vitro Determination of Cell Toxicity in HepG2 at 24 h

HepG2 cells (human hepatocellular carcinoma) were obtained from the American Type Culture Collection (ATCC) and cultured in Eagle's Minimum Essential Medium (Eagle) with Earle's balanced salt solution adjusted to contain 1.87 mM Glutamax™ I, 0.1 mM non-essential amino acids, 1.0 mM sodium pyruvate, 100000 U/L penicillin, 10000 μg/L streptomycin 90%; fetal bovine serum, 10%. Promega CellTiter 96® Aqueous Non-Radioactive Cell Viability Assay contains the tetrazolium compound [3-(4,5-dimethylthiazol-2-yl)-5-(3-carboxymethoxyphenyl)-2-(4-sulfophenyl)-2H-tetrazolium, inner salt (MTS). The conversion of MTS into the aqueous soluble formazan product is accomplished by dehydrogenase enzymes found in metabolically active cells. The quantity of formazan product is directly proportional to the number of living cells in culture.

Compounds were dissolved in DMSO to achieve an initial concentration of 100 mM. Serial dilutions were made from this stock solution into DMSO to achieve concentrations of 10, 1, 0.1 and 0.01 mM. The stock solution and serial dilutions were then diluted 1:100 with cell culture medium to obtain six final assay concentrations of 1000, 100, 10, 1, 0.1 and 0.01 µM. The final DMSO concentration in all wells was 1% v/v. HepG2 cells were incubated with test compounds for 24 hours. Relative cell viability was determined spectro-photometrically at 490 nm following the addition of the MTS dye and further one-hour incubation. Tamoxifen was used as the positive control.

The percent absorbance of the samples treated with the test article was compared to the untreated sample to calculate the percentage of control. The results of this test are given in Table 4.

TABLE 4

Determination of cell toxicity in HepG2

| Compound | 100 µM |
|---|---|
| Preparative example 2 | 107.19 |
| Preparative example 4 | 92.86 |
| Preparative example 6 | 84.31 |
| Preparative example 8 | 75.39 |
| Preparative example 10 | — |
| Indiplon | 69.8 |
| Zaleplon | 97.5 |
| Example 16 WO2005014597 | 53.2 |

Accordingly, the compounds from preparative examples 2, 4, 6 and 8 surprisingly show less cytotoxicity than prior art compounds, thus conferring a better safety profile to compounds of the present invention.

c) Metabolic Stability

In Vitro Determination of Metabolic Stability in Human Hepatocytes Cytosolic Fraction Compounds were dissolved in DMSO to achieve an initial concentration of 10 mM. This stock solution was then diluted with solvent and buffer to obtain final assay concentration of 5 µM. Compounds were tested at a single concentration of 5 µM in duplicate incubating with 1.0 mg/ml of pooled human cytosol (obtained from Xenotech plc) at 37° C. Metabolism was assessed in the presence or absence of cofactors and measured as loss of parent compound by LC/MS analysis at 0, 60 and 120-minutes time points. Percent parent remaining was then calculated. A generic LC method was used:

| Mobile phase: | A = 0.1% Formic acid in water |
| | B = 0.1% Formic acid in acetonitrile |
| HPLC Column: | Higgins Clipius C18 5 µm, 50 × 3 mm |
| Flow rate: | 2 ml · min⁻¹ |

| Gradient: | Time | % A | % B |
|---|---|---|---|
| | 0.00 | 95 | 5 |
| | 2.00 | 5 | 95 |
| | 2.50 | 5 | 95 |
| | 2.60 | 95 | 5 |
| | 3.00 | 95 | 5 |

The results of this test are given in Table 5.

TABLE 5

Metabolic stability in human hepatocyte cytosolic fraction

| Compound | 60 min | 120 min |
|---|---|---|
| Preparative example 2 | 104 | 110 |
| Preparative example 4 | 105 | 103 |
| Preparative example 6 | 103 | 106 |
| Indiplon | 100 | 98 |
| Zaleplon | 79 | 68 |

Surprisingly some compounds of the present invention show an increased metabolic stability comparatively to prior art compounds, thus predicting an improved pharmacokinetic profile for the instant compounds.

d) Pharmacokinetic Profile

In Vivo Determination of Pharmacokinetic Profile after Single Dose

The compound from preparative example 2 was tested for pharmacokinetic profile following intravenous administration. Indiplon was used as reference compound. Three male Sprague-Dawley rats, weighing 250-300 g were used for each compound. The sampling was performed by retroorbital sinus puncture at the following time points 2.5, 5, 30, 60, 120, 180, 300 and 420 min post-administration. The samples were kept in an ice-bath until plasma separation. The animals were anaesthetized by isoflurane inhaled at each extraction. Plasma was separated by centrifugation (10 min, 4° C., 4500 rpm) and stored at temperature below −70° C. until analysis.

An analytical method based on an extraction of each compound by liquid-solid extraction and subsequent determination by LC/MS or LC/MS/MS using an internal standard (IS) was used.

Calculation of pharmacokinetic parameters ($AUC_{0-t}$=area under the curve from zero to last extraction time-point, Cl=clearance, $t_{1/2}$=half-life and Vd=volume of distribution) according to non-compartmental analysis was performed. The results are shown in Table 6.

TABLE 6

Pharmacokinetic parameters

| Parameter | Compound | Mean |
|---|---|---|
| $AUC_{0-t}$ | Indiplon | 0.0007 |
| (g * hr/L) | Preparative example 2 | 0.0011 |
| Cl (L/hr/kg) | Indiplon | 3.4500 |
| | Preparative example 2 | 2.7442 |
| $t_{1/2}$ (hr) | Indiplon | 0.9837 |
| | Preparative example 2 | 1.7315 |
| Vd (L/kg) | Indiplon | 2.3206 |
| | Preparative example 2 | 7.2442 |

Experimental results exhibit a quite different pharmacokinetic profile for the compound of example 2 as compared to the prior art compound Indiplon. Indeed, the area under the curve is 57% higher for the compound of the preparative example 2, thus indicating an increased exposure to the product; clearance is 20% lower meanwhile its half-life is 76% higher, thus revealing a slower elimination rate; and finally volume of distribution is 212% higher, suggesting extensive distribution to deep non-aqueous compartments (ie brain) compared to indiplon. Pharmacokinetic parameters correlate with some animal pharmacology findings. For instance, in the in vivo sedative-hypnotic activity test in mice (3 μmol/kg po) the inhibition percentage decreases from 74% (5 minutes) to 67% (60 minutes) for indiplon, in contrast said parameter remains constant at 84% for the compound from preparative example 2. Said surprising pharmacokinetic properties show that the compound of the present invention affords a better sleep quality thus avoiding nocturnal awakenings and conferring a sounder and continued sleep.

The following non-limiting examples illustrate the scope of the present invention.

Preparative Example 1

N-[5-(3-Dimethylamino-acryloyl)-2-fluoro-phenyl]-N-methyl-acetamide 3.3 g (16.9 mmol) of N-(5-acetyl-2-fluoro-phenyl)-acetamide were dissolved in 8.36 ml (7.49 g) (62.89 mmol) of N,N-dimethylformamide dimethylacetal and the resultant solution was refluxed for 6.5 hours. The excess of volatile reagent was removed by reduced pressure distillation to yield a crude which was crystallized from ethyl acetate. 3.32 g of N-[5-(3-dimethylamino-acryloyl)-2-fluoro-phenyl]-acetamide as a yellowish-white solid were obtained (yield 78.6%).

$^1$H NMR (400 MHz, CDCl3): δ 2.21 (3H, s), 2.89 (3H, s), 3.11 (3H, s), 5.65 (1H, d, J=12.8 Hz), 7.05-7.1 (1H, m), 7.62-7.68 (2H, m), 7.77 (1H, d, J=12.4 Hz), 8.71-8.73 (1H, m).

MS (ES) m/z=251 (MH+)
HPLC=99.8%

1.5 g (5.99 mmol) of N-[5-(3-dimethylamino-acryloyl)-2-fluoro-phenyl]-acetamide were dissolved in 15 ml of dry N,N-dimethylformamide. To the solution formed at 0° C. and under inert atmosphere, 0.29 g (7.31 mmol) of sodium hydride were added. After stirring for 30 minutes, a solution of 0.94 g (6.59 mmol) of methyl iodide in 5 ml of dry N,N-dimethylformamide was added and stirring was maintained at room temperature for 5 h. The solvent was removed by reduced pressure distillation. To the resulting residue were added 30 ml of dichloromethane and 10 ml of water. The two layers were separated, and the aqueous layer was washed with 30 ml of dichloromethane. The organic layers were washed with 40 ml of water and dried over magnesium sulfate. The dichloromethane layer was evaporated to dryness to yield an oil which, crystallizing from ethyl acetate, gave 804 mg of N-[5-(3-dimethylamino-acryloyl)-2-fluoro-phenyl]-N-methyl-acetamide as a yellowish-white solid were obtained (yield 50.8%).

$^1$H NMR (400 MHz, CDCl3): δ 1.85 (3H, s), 2.94 (3H, s), 3.17 (3H, s), 3.22 (3H, s), 5.62 (1H, d, J=12.4 Hz), 7.16-7.25 (1H, m), 7.78-7.89 (3H, m).

MS (ES) m/z=265 (MH+)
HPLC=94.9%

Preparative Example 2

N-{2-Fluoro-5-[3-(thiophene-2-carbonyl)-pyrazolo[1,5-a]pyrimidin-7-yl]-phenyl}-N-methyl-acetamide A mixture of 0.073 g (0.38 mmol) of (5-amino-1H-pyrazol-4-yl)-thiophene-2-yl-methanone and 0.1 g (0.38 mmol) of N-[5-(3-dimethylamino-acryloyl)-2-fluoro-phenyl]-N-methyl-acetamide in 10 ml of glacial acetic acid was refluxed for 2.5 hours and then the solvent was removed by reduced pressure distillation. To the resulting residue were added 15 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 112 mg of N-{2-fluoro-5-[3-(thiophene-2-carbonyl)-pyrazolo[1,5-a]pyrimidin-7-yl]-phenyl}-N-methyl-acetamide as a solid (yield 75%).

$^1$H NMR (400 MHz, CDCl3): δ 1.98 (3H, s), 3.3 (3H, s), 7.13 (1H, d, J=4 Hz), 7.18-7.20 (1H, m), 7.42 (1H, t, J=8.8 Hz), 7.71 (1H, d, J=5.2 Hz), 8.02-8.08 (2H, m), 8.12 (1H, dd, J=2.4 and 7.6 Hz), 8.71 (1H, s), 8.82 (1H, d, J=4 Hz).

MS (ES) m/z=395 (MH+)
HPLC=99.2%
m.p.=165-167° C.

Preparative Example 3

N-[2-Chloro-5-(3-dimethylamino-acryloyl)-phenyl]-N-methyl-acetamide 4.46 g (21.1 mmol) of N-(5-acetyl-2-chloro-phenyl)-acetamide were dissolved in 10.4 ml (9.34 g) (78.39 mmol) of N,N-dimethylformamide dimethylacetal and the resultant solution was refluxed for 6.5 hours. The excess of volatile reagent was removed by reduced pressure distillation to yield a crude which was crystallized from ethyl acetate. 4.53 g of N-[2-chloro-5-(3-dimethylamino-acryloyl)-phenyl]-acetamide as a yellowish-white solid were obtained (yield 80.5%).

$^1$H NMR (400 MHz, CDCl3): δ 2.24 (3H, s), 2.90 (3H, s), 3.12 (3H, s), 5.66 (1H, d, J=12.4 Hz), 7.38 (1H, d, J=8.8 Hz), 7.62 (1H, d, J=8.8 Hz), 7.69 (1H, s), 7.77 (1H, d, J=12.4 Hz), 8.7 (1H, s).

MS (ES) m/z=267 (MH+)
HPLC=98.3%

1.0 g (3.75 mmol) of N-[2-chloro-5-(3-dimethylamino-acryloyl)-phenyl]-acetamide were dissolved in 10 ml of dry N,N-dimethylformamide. To the solution formed at 0° C. and under inert atmosphere, 0.18 g (4.57 mmol) of sodium hydride were added. After stirring for 30 minutes, a solution of 0.59 g (4.12 mmol) of methyl iodide in 3 ml of dry N,N-dimethylformamide was added and stirring was maintained at room temperature for 5 h. The solvent was removed by reduced pressure distillation. To the resulting residue were added 30 ml of dichloromethane and 10 ml of water. The two layers were separated, and the aqueous layer was washed with 30 ml of dichloromethane. The organic layers were washed with 40 ml of water and dried over magnesium sulfate. The dichloromethane layer was evaporated to dryness to yield an oil which, crystallizing from ethyl acetate-hexane, gave 928 mg of N-[2-chloro-5-(3-dimethylamino-acryloyl)-phenyl]-N-methyl-acetamide as a yellowish-white solid were obtained (yield 88.16%).

$^1$H NMR (400 MHz, CDCl3): δ 1.79 (3H, s), 2.94 (3H, s), 3.17 (3H, s), 3.19 (3H, s), 5.61 (1H, d, J=12.4 Hz), 7.50 (1H, d, J=8.4 Hz), 7.79-7.85 (3H, m).

MS (ES) m/z=281 (MH+)
HPLC=100%

Preparative Example 4

N-{2-Chloro-5-[3-(thiophene-2-carbonyl)-pyrazolo[1,5-a]pyrimidin-7-yl]-phenyl}-N-methyl-acetamide A mixture of 0.083 g (0.43 mmol) of (5-amino-1H-pyrazol-4-yl)-thiophene-2-yl-methanone and 0.12 g (0.43 mmol) of N-[2-chloro-5-(3-dimethylamino-acryloyl)-phenyl]-N-methyl-acetamide in 12 ml of glacial acetic acid was refluxed for 1.5 hours and then the solvent was removed by reduced pressure distillation. To the resulting residue were added 15 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 139 mg of N-{2-chloro-5-[3-(thiophene-2-carbonyl)-pyrazolo[1,5-a]pyrimidin-7-yl]-phenyl}-N-methyl-acetamide as a solid (yield 79%).

$^1$H NMR (400 MHz, CDCl3): δ 1.92 (3H, s), 3.27 (3H, s), 7.15 (1H, d, J=4.8 Hz), 7.19-7.21 (1H, m), 7.70-7.71 (1H, m), 7.73 (1H, d, J=8.8 Hz), 8.02 (1H, dd, J=2.4 and 7.6 Hz), 8.06-8.07 (1H, m), 8.12 8 (1H, d, J=2 Hz), 8.71 (1H, s), 8.83 (1H, d, J=4 Hz).

MS (ES) m/z=411 (MH+)
HPLC=99.6%
m.p.=191-193° C.

Preparative Example 5

N-[5-(3-Dimethylamino-acryloyl)-2-fluoro-phenyl]-N-methyl-methanesulfonamide 1.66 g (6.77 mmol) of N-(5-acetyl-2-fluoro-phenyl)-N-methyl-methanesulfonamide were dissolved in 3.35 ml (3.0 g) (25.18 mmol) of N,N-dimethylformamide dimethylacetal and the resultant solution was refluxed for 2.5 hours. The mixture was cooled at room temperature. To the solid formed was added 20 ml of n-hexane and filtered to yield a solid which was crystallized from ethyl acetate. 1.37 g of N-[5-(3-dimethylamino-acryloyl)-2-fluoro-phenyl]-N-methyl-methanesulfonamide as a yellowish-white solid were obtained (yield 67.4%).

$^1$H NMR (400 MHz, CDCl3): δ 2.92 (3H, s), 2.96 (3H, s), 3.15 (3H, s), 3.31 (3H, s), 5.61 (1H, d, J=12.8 Hz), 7.13-7.18 (1H, m), 7.78 (1H, d, J=12.8 Hz), 7.88-7.93 (2H, m).

MS (ES) m/z=301 (MH+)
HPLC=97.99%

Preparative Example 6

N-{2-Fluoro-5-[3-(thiophene-2-carbonyl)-pyrazolo[1,5-a]pyrimidin-7-yl]-phenyl}-N-methyl-methanesulfonamide A mixture of 0.064 g (0.33 mmol) of (5-amino-1H-pyrazol-4-yl)-thiophene-2-yl-methanone and 0.1 g (0.33 mmol) of N-[5-(3-dimethylamino-acryloyl)-2-fluoro-phenyl]-N-methyl-methanesulfonamide in 10 ml of glacial acetic acid was refluxed for 2.5 hours and then the solvent was removed by reduced pressure distillation. To the resulting residue were added 15 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 111 mg of N-[2-fluoro-5-[3-(thiophene-2-carbonyl)-pyrazolo[1,5-a]pyrimidin-7-yl]-phenyl]-N-methyl-methanesulfonamide as a solid (yield 77%).

$^1$H NMR (400 MHz, CDCl3): δ 3.01 (3H, s), 3.39 (3H, s), 7.13 (1H, d, J=4.4 Hz), 7.18-7.20 (1H, m), 7.36-7.41 (1H, m), 7.70 (1H, dd, J=1.2 and 5.2 Hz), 8.07-8.09 (1H, m), 8.11-8.17 (2H, m), 8.7 (1H, s), 8.80 (1H, d, J=4.8 Hz).

MS (ES) m/z=431 (MH+)
HPLC=98.6%
m.p.=194-196° C.

Preparative Example 7

N-[2-Chloro-5-(3-dimethylamino-acryloyl)-phenyl]-N-methyl-methanesulfonamide 1.0 g (4.04 mmol) of N-(5-acetyl-2-chloro-phenyl)-methanesulfonamide were dissolved in 10 ml of dry N,N-dimethylformamide and 2.69 ml (2.41 g) (20.19 mmol) of N,N-dimethylformamide dimethylacetal. The resultant solution was refluxed for 2 hours. The solvent and the excess of volatile reagent was removed by reduced pressure distillation to yield an oil which, in the presence of ethyl acetate, gave 1.04 of a crude. It was chromatographied (silica gel) using ethyl acetate/2-propanol as eluent. 0.51 g of N-[2-chloro-5-(3-dimethylamino-acryloyl)-phenyl]-N-methyl-methanesulfonamide as a yellowish-white solid were obtained (yield 40%).

$^1$H NMR (400 MHz, CDCl3): δ 2.9 (3H, s), 3.04 (3H, s), 3.15 (3H, s), 3.3 (3H, s), 5.61 (1H, d, J=12.4 Hz), 7.48 (1H, d, J=8.4 Hz), 7.78 (1H, d, J=12.8 Hz), 7.83 (1H, dd, J=8.8-1.6 Hz), 7.93 (1H, d, J=1.6 Hz).

MS (ES) m/z=317 (MH+)
HPLC=87.58%

Preparative Example 8

N-{2-Chloro-5-[3-(thiophene-2-carbonyl)-pyrazolo[1,5-a]pyrimidin-7-yl]-phenyl}-N-methyl-methanesulfonamide A mixture of 0.076 g (0.39 mmol) of (5-amino-1H-pyrazol-4-yl)-thiophene-2-yl-methanone and 0.124 g (0.39 mmol) of (N-[2-chloro-5-(3-dimethylamino-acryloyl)-phenyl]-N-methyl-methanesulfonamide in 10 ml of glacial acetic acid was refluxed for 1.5 hours and then the solvent was removed by reduced pressure distillation. To the resulting residue were added 15 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 128 mg of N-{2-chloro-5-[3-(thiophene-2-carbonyl)-pyrazolo[1,5-a]pyrimidin-7-yl]-phenyl}-N-methyl-methanesulfonamide as a solid (yield 73%).

$^1$H NMR (400 MHz, CDCl3): δ 3.09 (3H, s), 3.38 (3H, s), 7.15 (1H, d, J=4.8 Hz), 7.19-7.20 (1H, m), 7.68-7.71 (2H, m), 8.07-8.09 (2H, m), 8.19 (1H, d, J=2 Hz), 8.71 (1H, s), 8.82 (1H, d, J=4.4 Hz).

MS (ES) m/z=447 (MH+)
HPLC=98.1%
m.p.=241-243° C.

Preparative Example 9

N-[5-(3-Dimethylamino-acryloyl)-2-fluoro-phenyl]-N-prop-2-ynyl-methanesulfonamide 1.2 g (4.46 mmol) of N-(5-acetyl-2-fluoro-phenyl)-N-prop-2-ynyl-methanesulfonamide were dissolved in 3 ml (2.7 g) (22.58 mmol) of N,N-dimethylformamide dimethylacetal and the resultant solution was refluxed for 2.5 hours. The mixture was cooled at room temperature and 20 ml of n-hexane were added. The oil obtained was chromatographied (silica gel) using ethyl acetate/2-propanol as eluent. 0.46 g of a yellowish-white solid were obtained. This solid was crystallized in ethyl acetate and 0.213 g of N-[5-(3-dimethylamino-acryloyl)-2-fluoro-phenyl]-N-prop-2-ynyl-methanesulfonamide were obtained (yield 14.7%).

$^1$H NMR (400 MHz, CDCl3): δ 2.35 (1H, m), 2.92 (3H, s), 3.11 (3H, s), 3.15 (3H, s), 4.43 (2H, m), 5.61 (1H, d, J=12.8 Hz), 7.16-7.21 (1H, m), 7.79 (1H, d, J=12.8 Hz), 7.91-7.94 (1H, m), 8.01-8.04 (1H, m).

MS (ES) m/z=325 (MH+)
HPLC=91.63%

Preparative Example 10

N-{2-Fluoro-5-[3-(thiophene-2-carbonyl)-pyrazolo[1,5-a]pyrimidin-7-yl]-phenyl}-N-prop-2-ynyl-methanesulfonamide A mixture of 0.108 g (0.56 mmol) of (5-amino-1H-pyrazol-4-yl)-thiophene-2-yl-methanone and 0.198 g (0.61 mmol) of N-[5-(3-dimethylamino-acryloyl)-2-fluoro-phenyl]-N-prop-2-ynyl-methanesulfonamide in 10 ml of glacial acetic acid was refluxed for 2 hours and then the solvent was removed by reduced pressure distillation. To the resulting residue were added 15 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 156 mg of N-{2-fluoro-5-[3-(thiophene-2-carbonyl)-pyrazolo[1,5-a]pyrimidin-7-yl]-phenyl}-N-prop-2-ynyl-methanesulfonamide as a solid (yield 61%).

$^1$H NMR (400 MHz, CDCl3): δ 2.39 (1H, s), 3.16 (3H, s), 4.50 (2H, s), 7.14 (1H, d, J=4.4 Hz), 7.18-7.20 (1H, m), 7.40-7.44 (1H, m), 7.70 (1H, m), 8.07-8.09 (1H, m), 8.18-8.21 (1H, m), 8.24-8.26 (1H, m), 8.7 (1H, s), 8.80 (1H, d, J=4.8 Hz).

MS (ES) m/z=455 (MH+)
HPLC=94.9%
m.p.=149-153° C.

Composition Example 1

5 mg Tablets

| | |
|---|---|
| Compound of preparative example 2 | 5.0 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Composition Example 2

10 mg Capsules

| | |
|---|---|
| Compound of preparative example 2 | 10.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline cellulose q.s. to | 155.0 mg |

Composition Example 3

Oral Drops

| | |
|---|---|
| Compound of preparative example 2 | 0.5 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 ml |
| Purified water q.s. to | 100.0 ml |

Composition Example 4

2.5 mg Tablets

| | |
|---|---|
| Compound of preparative example 2 | 2.5 mg |
| Colloidal silicon dioxide | 0.6 mg |
| Croscaramellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Composition Example 5

5 mg Capsules

| | |
|---|---|
| Compound of preparative example 2 | 5.0 mg |
| Colloidal silicon dioxide | 0.6 mg |
| Crospovidone | 12.0 mg |
| Talc | 4.0 mg |

-continued

| | |
|---|---|
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline q.s. to | 155.0 mg |

Composition Example 6

Oral Drops

| | |
|---|---|
| Compound of preparative example 2 | 0.25 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 ml |
| Purified q.s. to | 100.0 ml |

The invention claimed is:

1. A method for treating insomnia in a mammal which comprises administering to said mammal an effective amount of a compound of formula (I):

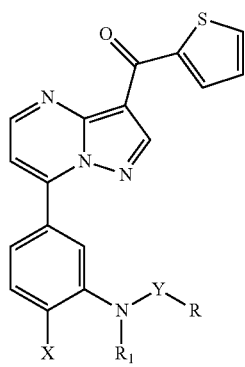

wherein
R represents an alkyl($C_1$-$C_6$);
$R_1$ is selected from the group consisting of alkyl($C_1$-$C_6$) and alkynyl($C_1$-$C_6$);
X represents a halogen atom; and
Y is selected from the group consisting of —CO— and —$SO_2$—; or a pharmaceutically acceptable salt thereof,
wherein the effective amount of the compound to be administered is a total daily dose of 5 mg to 10 mg.

2. A method for treating insomnia in a mammal which comprises administering to said mammal an effective amount of a compound of formula (I):

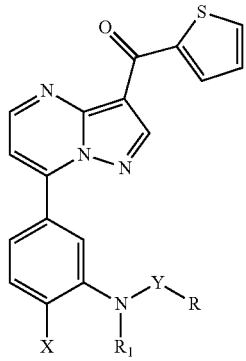

wherein
R represents an alkyl($C_1$-$C_6$);
$R_1$ is selected from the group consisting of alkyl($C_1$-$C_6$) and alkynyl($C_1$-$C_6$);
X represents a fluorine atom; and
Y is selected from the group consisting of —CO— and —$SO_2$—; or a pharmaceutically acceptable salt thereof,
wherein the effective amount of the compound to be administered is a total daily dose of 5 mg to 10 mg.

3. The method of claim 1, wherein X represents a chlorine atom.

4. The method of claim 1, wherein the effective amount of the compound to be administered is a total daily dose of 5 mg.

5. The method of claim 1, wherein the effective amount of the compound to be administered is a total daily dose of 10 mg.

6. The method of claim 2, wherein the effective amount of the compound to be administered is a total daily dose of 5 mg.

7. The method of claim 2, wherein the effective amount of the compound to be administered is a total daily dose of 10 mg.

8. A method for increasing duration of sleep in a mammal which comprises administering to said mammal an effective amount of a compound of formula (I):

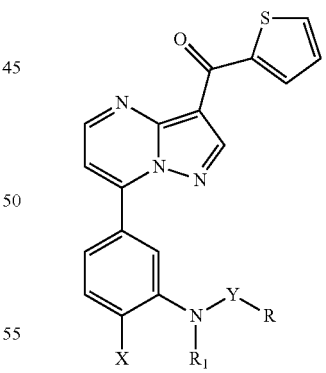

wherein
R represents an alkyl($C_1$-$C_6$);
$R_1$ is selected from the group consisting of alkyl($C_1$-$C_6$) and alkynyl($C_1$-$C_6$);
X represents a halogen atom; and
Y is selected from the group consisting of —CO— and —$SO_2$—; or a pharmaceutically acceptable salt thereof.

* * * * *